US012017034B2

United States Patent
Albertsen et al.

(10) Patent No.: US 12,017,034 B2
(45) Date of Patent: Jun. 25, 2024

(54) SINGLE USE CAP WITH SLEEVE AND CARRIER FOR NEEDLELESS CONNECTORS

(71) Applicant: Quest Medical, Inc., Allen, TX (US)

(72) Inventors: Jeffrey Albertsen, McKinney, TX (US);
Robert Mart, Colleyville, TX (US);
Andrew Nelson, Dallas, TX (US);
James Bernal, Frisco, TX (US)

(73) Assignee: Quest Medical, Inc., Allen, TX (US)

( * ) Notice: Subject to any disclaimer, the term of this patent is extended or adjusted under 35 U.S.C. 154(b) by 234 days.

(21) Appl. No.: 17/541,647

(22) Filed: Dec. 3, 2021

(65) Prior Publication Data

US 2023/0173245 A1    Jun. 8, 2023

(51) Int. Cl.
*A61M 39/20*    (2006.01)
*A61M 5/30*    (2006.01)
*A61M 39/16*    (2006.01)

(52) U.S. Cl.
CPC .............. *A61M 39/20* (2013.01); *A61M 5/30* (2013.01); *A61M 39/16* (2013.01)

(58) Field of Classification Search
CPC ..... A61M 39/20; A61M 39/16; A61M 39/165
See application file for complete search history.

(56) References Cited

U.S. PATENT DOCUMENTS

| 5,902,298 | A | 5/1999 | Niedospial, Jr. et al. |
| 5,921,419 | A | 7/1999 | Niedospial, Jr. et al. |
| 2005/0119521 | A1* | 6/2005 | Pitcher ...................... A61F 5/41 600/38 |
| 2016/0143647 | A1* | 5/2016 | Gavriely ............ A61B 17/1322 606/203 |
| 2021/0322752 | A1 | 10/2021 | Jiang et al. |
| 2021/0346672 | A1 | 11/2021 | Grant et al. |

* cited by examiner

*Primary Examiner* — Bradley J Osinski
(74) *Attorney, Agent, or Firm* — Stephen Y. Liu; Carstens, Allen & Gourley, LLP

(57) ABSTRACT

A single use cap for connectors and corresponding method of use. The single use cap has a carrier with a body including a base that defines an opening separated from an end wall by a side wall. The opening leads into a cavity sized to receive a connector head. The single use cap also has an elastomeric sleeve releasably coupled to the carrier to span the opening. The elastomeric sleeve is configured to be transferred to the connector upon insertion of the head through the opening and at least partially into the cavity.

20 Claims, 13 Drawing Sheets

SINGLE USE CAP WITH SLEEVE AND CARRIER FOR NEEDLELESS CONNECTORS

BACKGROUND

Technical Field

Novel aspects of the present disclosure relate to the field of medical devices. More particularly, and not by way of limitation, the present disclosure is directed to a single use single use cap for connectors.

Background

Needleless connectors (NCs) are transitional interfaces that permit the exchange of fluids between containers, fluid transfer devices, and/or fluid conduits. NCs were designed primarily for use in the medical field to prevent needlestick injuries to medical care professionals. The NCs are typically attached to the ends of vascular catheters or other tubular structures, such as branched intravenous (IV) lines, to facilitate access for infusion and aspiration without the need for needles.

NCs generally have a housing that define a fluid pathway between a distal end to a proximal end. For some NCs, the proximal end is configured to engage with a fluid distribution line, such as a catheter or IV, and the distal end is exposed to the environment and configured to engage with fluid transfer device, such as a syringe, or fluid sources, such as a vial. For other NCs, the proximal end is configured to engage with a fluid source, such as a vial, and the distal end is exposed to the environment and configured to engage with a fluid transfer device. The fluid pathway, which extends axially through the NC, is typically sealed by a movable septum at the distal end to prevent entry of pathogens or contaminants into the NC. The pathogens or contaminants could then proceed into the fluid distribution line before entering into the patient's body, causing infection. Alternatively, the pathogens or contaminants could proceed into the fluid source, which would result in contamination. Disinfection of the septum before attaching the fluid source to the NC is crucial for reducing the rate of preventable infections in medical care facilities.

SUMMARY OF THE INVENTION

Novel aspects of the present disclosure are directed to a single use cap for use with a connector head. In a non-limiting embodiment, the connector head can be the head of a needleless connector (NC). The single use cap has a carrier with a body including a base that defines an opening separated from an end wall by a side wall. The opening leads into a cavity sized to receive a connector head. The single use cap also has an elastomeric sleeve releasably coupled to the carrier to span the opening. The elastomeric sleeve is configured to be transferred to the connector head upon insertion of the head through the opening and at least partially into the cavity.

Novel aspects of the present disclosure are also directed to a method using a single use cap that includes an elastomeric sleeve releasably coupled to a carrier having a body including a base defining an opening that is separated from an end wall by a side wall, the opening leading into a cavity sized to receive a connector head. The method includes the steps of exposing the elastomeric sleeve spanning the opening at the base of the carrier, aligning the connector head with the opening at the base of the carrier, and inserting the connector head through the opening at the base of the carrier and into the cavity to cause the elastomeric sleeve to disengage from the carrier and transfer to the connector head.

Other aspects, embodiments and features of the invention will become apparent from the following detailed description of the invention when considered in conjunction with the accompanying figures. In the figures, each identical, or substantially similar component that is illustrated in various figures is represented by a single numeral or notation. For purposes of clarity, not every component is labeled in every figure. Nor is every component of each embodiment of the invention shown where illustration is not necessary to allow those of ordinary skill in the art to understand the invention.

BRIEF DESCRIPTION OF THE FIGURES

The novel features believed characteristic of the invention are set forth in the appended claims. The invention itself, however, as well as a preferred mode of use, further objectives and advantages thereof, will be best understood by reference to the following detailed description of illustrative embodiments when read in conjunction with the accompanying figures, wherein:

DETAILED DESCRIPTION

Needleless connectors have been identified as a cause of catheter-related bloodstream infection (CRBSI). Inadequate disinfection of NCs allows pathogens to enter a patient's bloodstream, resulting in an expensive and time-consuming road to recovery. The average costs for treating CBRSI is about $48,000, with an increase in the length of stay (LoS) at the hospital by about 7 days. Patients suffering from CBRSI are 5 times more likely to be readmitted to the hospital and experience a 10% increase in mortality rate.

To combat CBRSI, specific disinfection guidelines have been implemented. For example, the current guidelines for engaging needleless connectors (NCs) are as follows: for every engagement, scrub the surface of the NC with an alcohol wipe for 30 seconds, allow the NC to dry for 20 seconds, and then cap the NC when not engaged. In another example, the current guidelines for intravenous (IV) line access with a regular cap are as follows: remove cap, disinfect the exposed surfaces of the needleless connector, connect syringe with saline to check patency, disconnect the syringe, clean the needleless connector again, connect syringe or IV set with medication and deliver, disconnect the syringe or IV, clean the needleless connector again, connect syringe with saline to flush, and disconnect and place a new cap on the needleless connector.

These current disinfection guidelines of complex. Compliance with these guidelines can vary due to subjective interpretation of the steps, and due to events occurring within specific medical settings. For example, the manual disinfection with the alcohol wipe can include multiple steps over multiple interfaces. Time constraints are sometimes not followed. Additionally, single-use caps are sometimes reused, particularly when replacement caps are not available. Sometimes caps are improperly attached or not used at all. Even with conventional single-use disinfection caps that purport to eliminate the need to disinfect the NC prior to use suffers from user error. For example, some medical care providers continue to disinfect the NC because they do not know if it was previously attached correctly, or if it was removed and reused. Thus, novel aspects of the present disclosure recognize the need for a single use cap that self-modifies to prevent reuse to eliminate the uncertainty faced by medical care providers.

While the various embodiments described in this disclosure depict use of the single use cap with needleless connectors, the illustrative use should be deemed exemplary and non-limiting. The single use caps described herein can be applied equally to connector heads, fittings, or other openings for vessels and fluid conduits in the medical field, as well as in non-medical industries.

Figure 1:
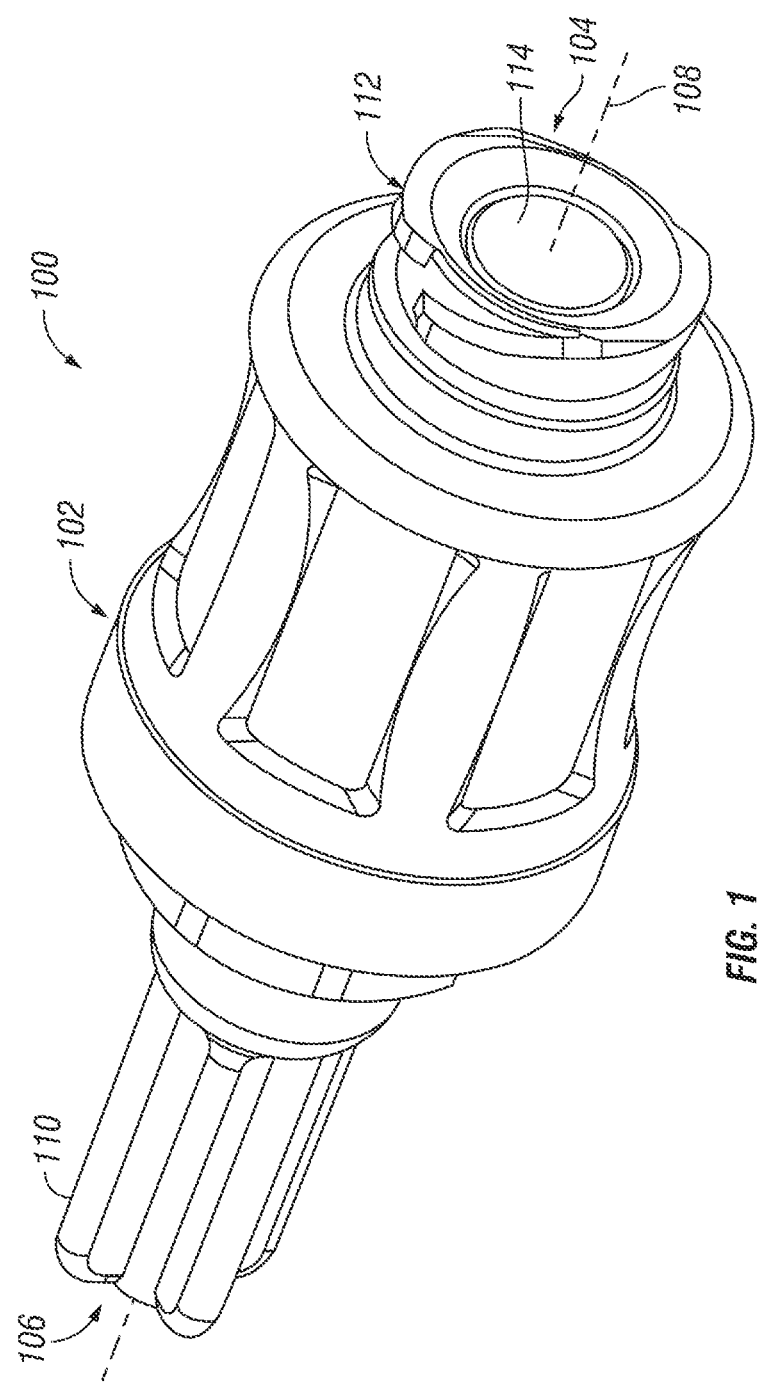
FIG. 1 is a perspective view of a needleless connector.

FIG. 1 is a perspective view of an exemplary needleless connector. When attached to a terminal end of a fluid conduit, such as an IV or catheter, the NC 100 selectively seals the fluid conduit to prevent ingress of pathogens and contaminants when not actively in use, but which can permit infusion or aspiration of fluids as required.

The NC 100 includes a housing 102 having a distal end 104 and a proximal end 106. The NC 100 defines a fluid pathway between the distal end 104 and the proximal end 106, coinciding with the axis 108. A tail 110 at the proximal end 106 is configured to engage with a tube (not shown). In this example in FIG. 1, the tail 110 is a narrow, elongated structure configured to be frictionally fit inside of a receiver, such as the terminal end of a tube. A head 112 projects outwardly from the housing 102 at the distal end 104 and is configured to be removably engaged with a receiving end of a fluid transfer device (not shown), such as a syringe, or a fluid dispenser, such as an IV bag or vial (also not shown). In this example in FIG. 1, a threaded interface is disposed on the exterior surface of the head 112 of the NC 100, which is configured to engage a threaded, interior sidewall of the fluid transfer device. In a non-limiting embodiment, the threaded interface of NC 100 is a luer lock fitting.

To prevent the ingress of pathogens into the attached tube via the NC 100, the fluid pathway can be sealed by a movable septum 114 that is partially exposed at distal end 104 of the NC. In one embodiment, the movable septum 114 is an exposed surface of a compressible valve housed within the housing 102. When the compressible valve is exposed to a compression force, the septum 114 disengages from the distal end 104 of the NC 100 to expose an opening that allows fluid to pass from a fluid dispenser through the NC 100 and into the attached tube. The compression force is generally applied to the septum 114 by attachment of a fluid transfer device or fluid source to the head 112 of the NC 100, causing the fluid transfer device or fluid source to engage with the septum 114, unsealing the septum 114 from the distal end 104 of the NC 100.

Figure 2:
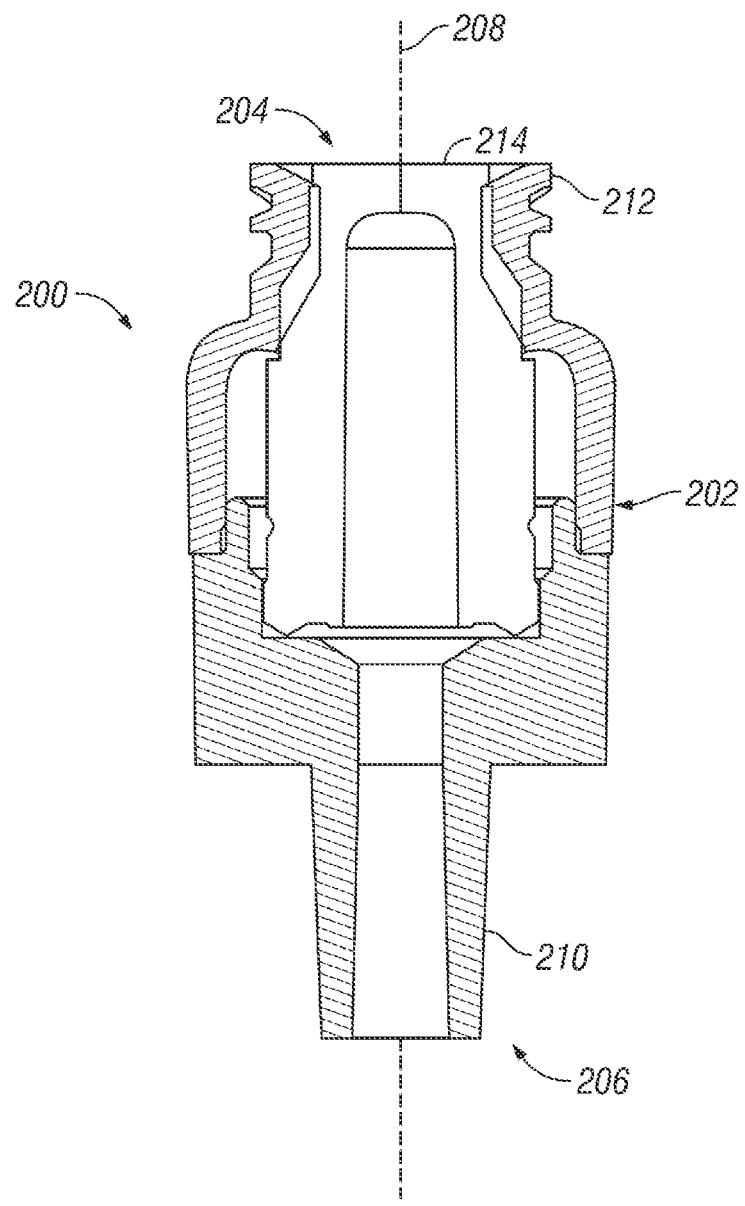
FIG. 2 is a partial cutaway side view of another exemplary needleless connector.

FIG. 2 is a partial cross-sectional view of another exemplary needleless connector. The NC 200 is configured to attach to and selectively seal containers of liquid, e.g., vials, or fluid conduits, such as IVs, to prevent ingress of pathogens when not in use. The NC 200 can permit infusion or aspiration of fluids as required.

The NC 200 includes a housing 202 having a distal end 204 and a proximal end 206. The NC 200 defines a fluid pathway between the distal end 204 and the proximal end 206, coinciding with the axis 208. A tail 210 at the proximal end 206 of the NC 200 is configured to be engaged with a fluid conduit, such as an IV (not shown), or fluid source, such as a container (not shown). A head 212 projects outwardly from the housing 202 at the distal end 204 and is configured to be removably engaged with a receiving end of a fluid transfer device (not shown), such as a syringe. In this example in FIG. 2, a threaded interface is disposed on the exterior surface of the head 212 of the NC 200, which is configured to engage a threaded, interior sidewall of the fluid transfer device. In a non-limiting embodiment, the threaded interface of NC 200 is a luer lock fitting.

To prevent the ingress of pathogens into the attached tube via the NC 200, the fluid pathway can be sealed by a movable septum 214 that is partially exposed at distal end 204 of the NC. In one embodiment, the movable septum 214 is an exposed surface of a compressible valve housed within the housing 202. When the compressible valve is exposed to a compression force, the septum 214 disengages from the distal end 204 of the NC 200 to expose an opening that allows fluid to pass from a fluid dispenser through the NC 200 and into the attached tube. The compression force is generally applied to the septum 214 by attachment of a fluid transfer device to the head 212 of the NC 200, causing the fluid transfer device or fluid source to engage with the septum 214, unsealing the septum 214 from the distal end 204 of the NC 200.

Figure 3A:
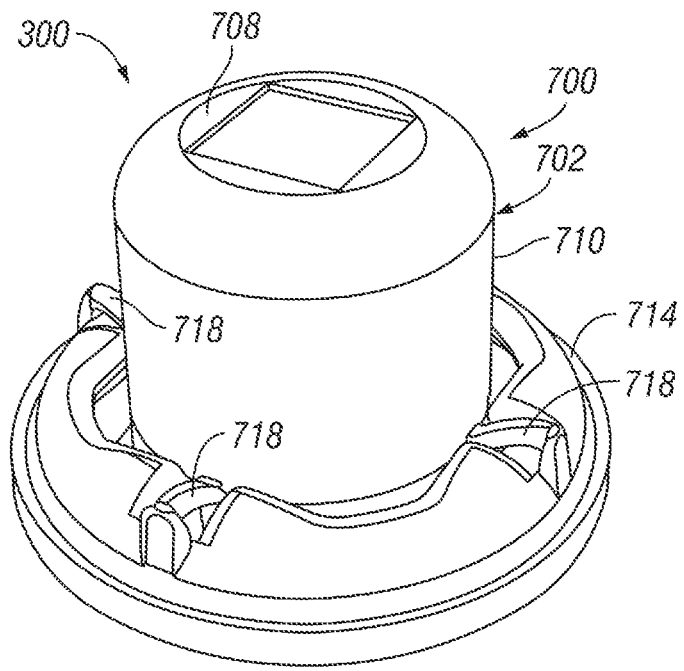
FIGS. 3A-3C are schematic diagrams showing various views of a single use cap for use with a needleless connector in accordance with an illustrative embodiment.
Figure 3B:
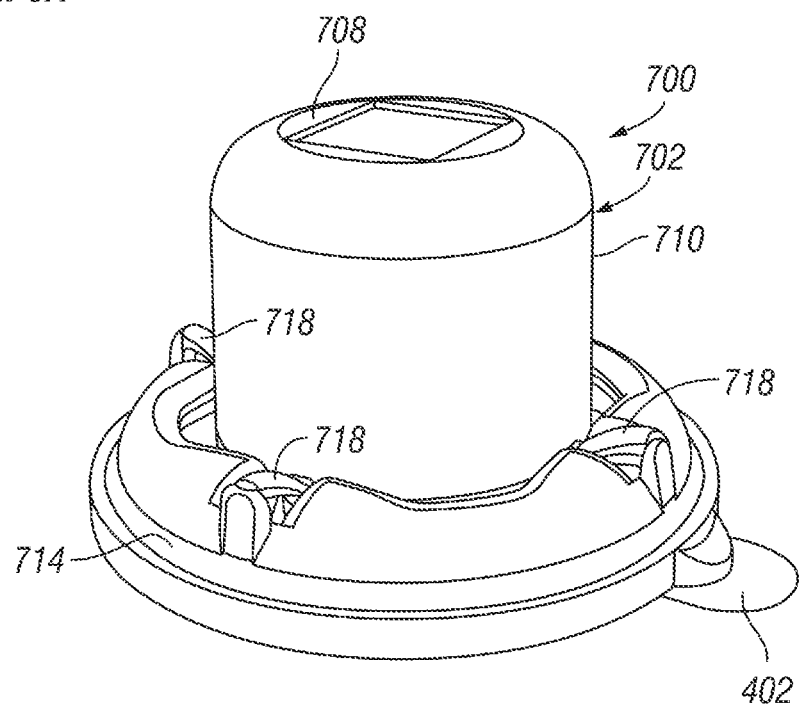
Figure 3C:
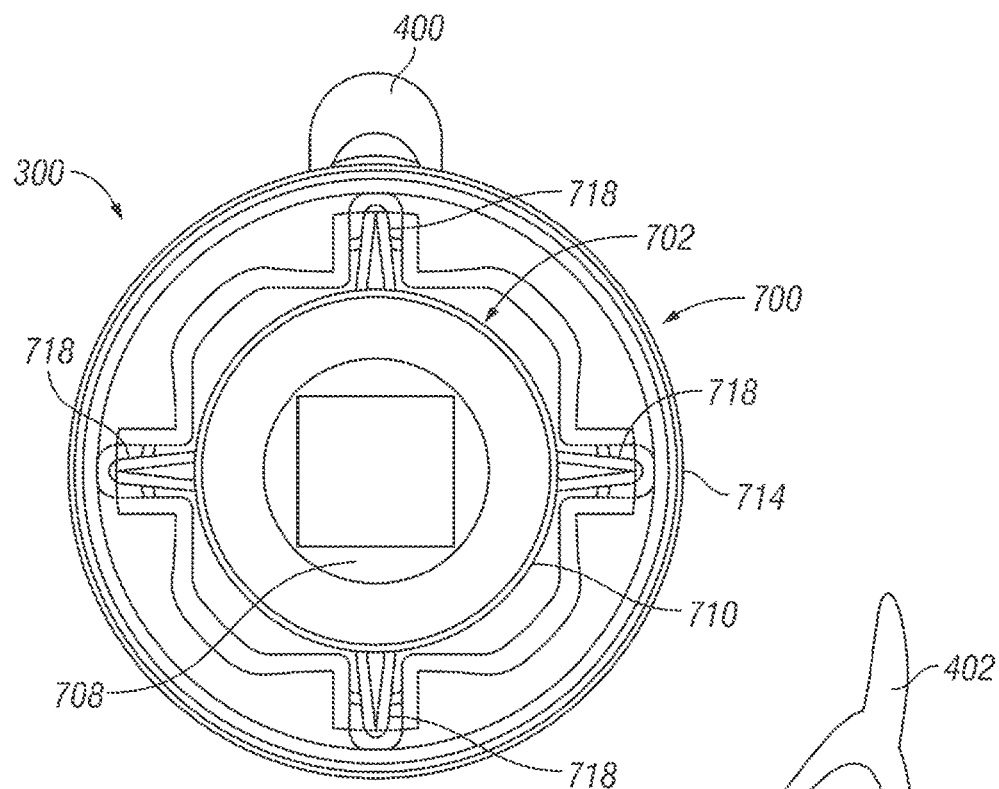

FIGS. 3A-3C are schematic diagrams showing various views of a single use cap usable with a needleless connector in accordance with an illustrative embodiment. In particular, FIG. 3A is a perspective view of the single use cap 300 and FIG. 3B is another perspective view of the single use cap 300, rotated approximately 90 degrees axially. FIG. 3C is a plan view of the single use cap 300. For the sake of simplicity, the view presented in FIG. 3C will be referred to as the top view and a view presented from the opposite side will be referred to as the bottom view.

Novel aspects of the single use cap 300 include features that reduce CRBSI by preventing re-use of the elastomeric sleeve 800. With particular reference to FIG. 3A, the single use cap 300 includes a carrier 700 with a body 702 including a base 704 defining an opening 706, shown in more detail in FIG. 7, which is separated from an end wall 708 by a side wall 710. The opening 706 leads into a cavity 712, shown in more detail in FIG. 6, which is sized to receive a head of a NC, such as head 112 of NC 100 in FIG. 1. In this example in FIG. 3, the body 702 of the single use cap 300 is generally cylindrical and can be formed from a rigid polymer to protect an elastomeric sleeve 800 housed by the carrier 700.

Figure 4:
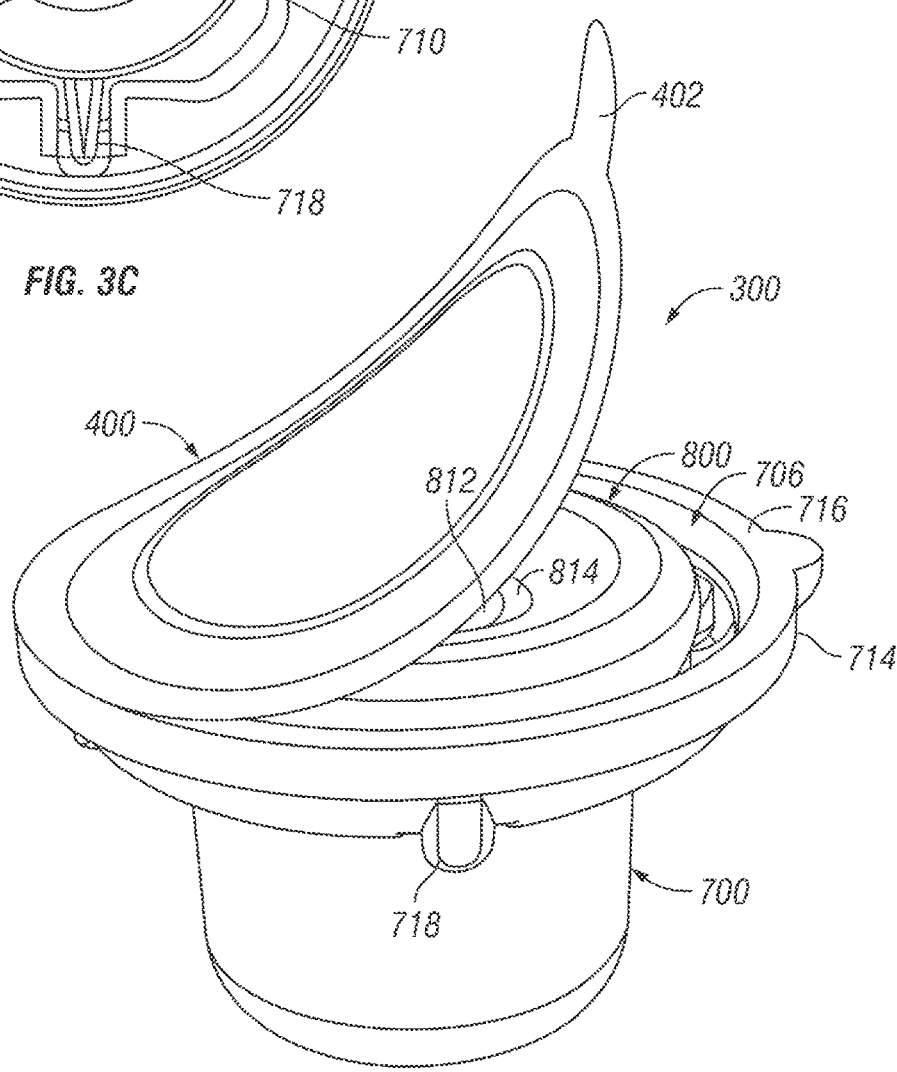
FIG. 4 is another perspective view of the single use cap with the sealing membrane partially removed according to an illustrative embodiment.
Figure 5:
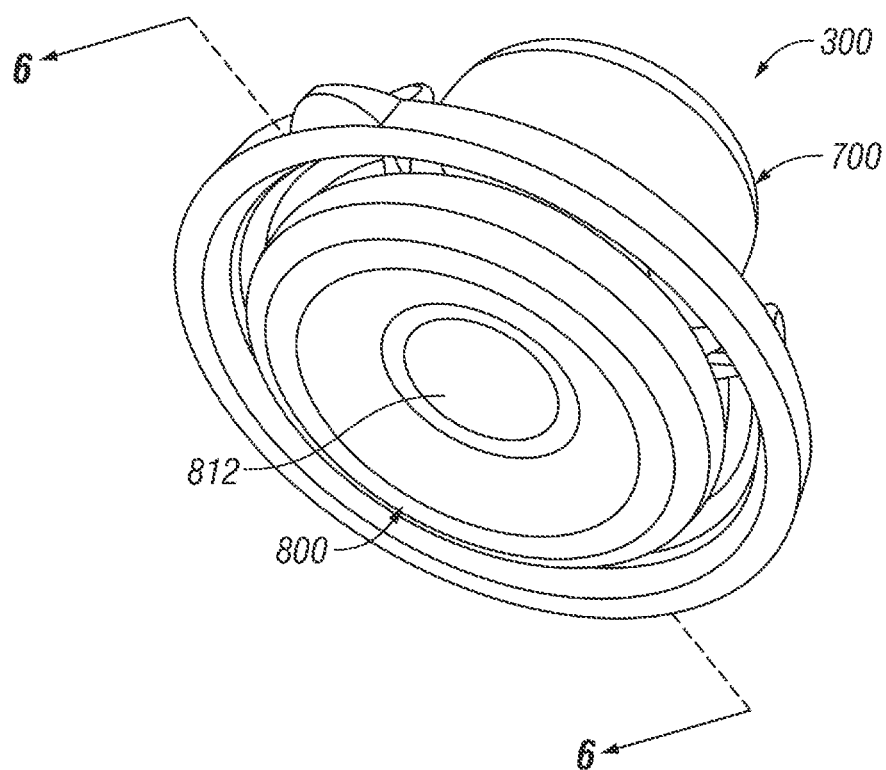
FIG. 5 is another perspective view of the single use cap showing the elastomeric sleeve mounted to the carrier in accordance with an illustrative embodiment.

The elastomeric sleeve 800, which is depicted in more detail in FIG. 8, is releasably coupled to the carrier 700 to span the opening 706, as shown in more detail in FIG. 5. The elastomeric sleeve 800 is configured to be transferred to the head of the NC upon insertion of the head through the opening 706 and at least partially into the cavity 712. To protect the elastomeric sleeve 800 from contamination, the opening 706 of the single use cap 300 and at least the distal end of the elastomeric sleeve 800 are sealed by a sealing membrane 400, as shown in more detail in FIG. 4, adhered to a sealing ring 714. To facilitate removal of the sealing membrane 400, a grasping tab 402 is provided which extends outwardly from the sealing membrane 400 and the sealing ring 714.

The sealing ring 714 is a generally annular structure circumscribing the body 702 of the carrier 700 proximate to the base 704. The sealing ring 714 has a sealing surface 716, shown in more detail in FIG. 4, which is adhered to the sealing membrane 400. In some embodiments, the sealing ring 714 is connected to the body 702 by a set of connecting arms 718. As used herein, the term "set" means one or more. Thus, "a set of connecting arms" can be a single connecting arm or two or more connecting arms. In the non-limiting embodiment depicted in FIG. 3, the set of connecting arms 718 includes four connecting arms arranged equidistantly around the base 704 of the body 702. Each of the set of connecting arms 718 can be a flexing member that permits the sealing ring 714 to translate axially relative to the body 702 in response to receiving a depressing force. As described in more detail in FIG. 6 that follows, the depressing force is in a direction from the end wall 708 towards the base 704 to cause a set of sleeve ejecting edges 720 extending radially inward from the sealing ring 714 to engage with the elastomeric sleeve 800. Engagement of the set of sleeve ejecting edges 720 with the elastomeric sleeve 800 urges the elastomeric sleeve 800 to elongate, which in turn causes the elastomeric sleeve 800 to disengage from the carrier 700.

FIG. 4 is another perspective view of the single use cap with the sealing membrane partially removed according to an illustrative embodiment. In particular, the single use cap 300 is shown from the bottom perspective view with the sealing membrane 400 partially removed from the sealing ring 714 to partially expose the elastomeric sleeve 800 mounted to the carrier 700. As can be seen, the sealing membrane 400 can be in a generally coextensive arrangement with the footprint of the sealing ring 714 to reduce the likelihood of inadvertent unsealing.

The sealing membrane 400 can provide a hermetically sealed environment to prevent contamination of the interior surfaces of the elastomeric sleeve 800 that can come into contact with the head of the NC (or other openings), and to prevent evaporation of disinfectant provided with the disinfectant applicator 812 secured with the elastomeric sleeve 800 by a retaining ring 814. Thus, the sealing membrane 400 can be formed from materials that are impermeable, or substantially impermeable, to air and moisture. In some embodiments, the sealing membrane 400 is formed from foil, from plastic, or combinations thereof and adhered to the sealing surface 716 of the sealing ring 714 using conventionally available adhesives.

In embodiments where the sealing ring 714 is attached to the body 702 of the carrier 700 by a set of connecting arms 718, as can be seen in more detail in FIG. 3C, a gap is maintained between the sealing ring 714 and body 702 of the carrier 700 to allow for axial movement of the sealing ring 714 relative to the body 702. Thus, even if the sealing membrane 400 is adhered to the sealing surface 716 of the sealing ring 714 to seal the bottom of the single use cap 300, the gap provides a means of vapor exchange, i.e., evaporation, and ingress for contaminants. In some embodiments, to achieve a hermetically sealed environment to prevent contamination and evaporation, when the sealing membrane 400 is adhered to the sealing surface 716, the sealing membrane 400 is also sealed against the inner surface of the elastomeric sleeve 800 that is exposed at the bottom of the single use cap 300.

FIG. 5 is another perspective view of the single use cap 300 showing the elastomeric sleeve 800 mounted to the carrier 700 in accordance with an illustrative embodiment. The elastomeric sleeve 800 is exposed once the sealing membrane 400 is removed the sealing surface 716 of the sealing ring 714. Once the sealing membrane 400 is removed, the interior surface of the elastomeric sleeve 800 is exposed. The interior surface of the elastomeric sleeve 800 is the portion that comes into contact with the head of the NC once the elastomeric sleeve 800 is disengaged from the carrier 700.

The elastomeric sleeve 800 is secured to the carrier 700 in a shortened configuration that is shorter than the elastomeric sleeve 800 when fully elongated. In a particular embodiment, the elastomeric sleeve 800 achieves the shortened configuration by rolling the elastic sidewall 806 outwardly and upwardly, as shown in FIG. 6, to achieve a flattened, toroidal-like structure with the disinfectant applicator 812 in the middle.

Figure 6:
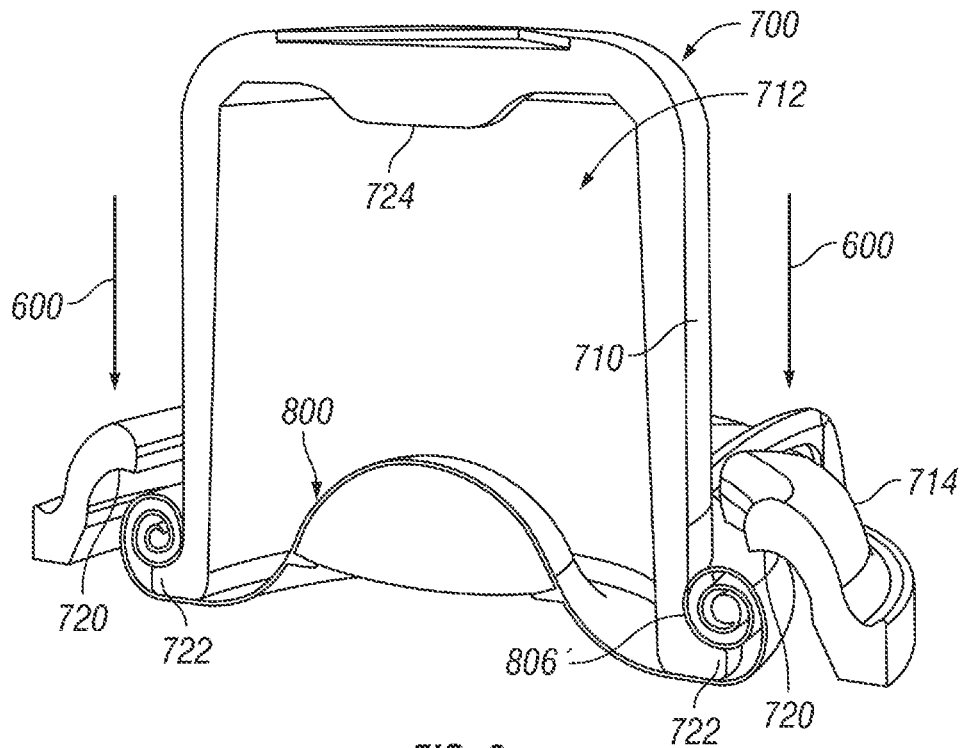
FIG. 6 is a cross-sectional view of the single use cap according to an illustrative embodiment.

FIG. 6 is a cross-sectional view of the single use cap 300 according to an illustrative embodiment. The cross-sectional view is of the single use cap 300 shown in FIG. 5 and taken along line 6-6. The single use cap 300 is formed from a carrier 700 having a body 702 and a sealing ring 714 connected to the body 702 by a set of connecting arms 718 as shown in more detail in FIGS. 7A-7B. At the base 704 of the body 702 is an opening 706 that leads into a cavity 712.

The elastomeric sleeve 800 is releasably coupled to the carrier 700 to span the opening 706. In one embodiment, the elastomeric sleeve 800 is rolled up and the rolled edge 806' of the elastic sidewall 806 is coupled to one or more flange structures 722 that project outwardly from the sidewall 710 of the carrier 700 at the base 704. The elastomeric sleeve 800 is transferred from the carrier 700 to the head of an NC by aligning the head of the NC with the opening 706 in the base 704 of the carrier 700 and inserting the head into the cavity 712, which causes the head of the NC to contact the inner surface of the elastic side wall 806 of the elastomeric sleeve 800. As the head of the NC travels axially towards the end wall 708, the elastomeric sleeve 800 elongates as the head of the NC exerts a force on the elastomeric sleeve in the axial direction. The force imparted upon the elastomeric sleeve 800 can cause the rolled edge 806' of the elastic sidewall 806 to begin to unroll, which initiates the process of transferring from the carrier 700 to the head of the NC. In some embodiments, by the time the head of the NC reaches the end wall 708 of the body 702 of the carrier 700, the elastomeric sleeve 800 has elongated fully or sufficiently to cause the elastomeric sleeve 800 to disengage from the one or more flange structures 722 and onto the head of the NC. When the elastomeric sleeve 800 is transferred to the head of the NC, the elastomeric sleeve 800 is frictionally fit to the head of the NC, securing the opening in the head of the NC within the elastomeric sleeve 800.

In some embodiments, when the head of the NC is brought into contact with the end wall 708 of the body 702 of the carrier 700, the disinfectant applicator 812 shown in FIG. 5 is compressed between the head of the NC and the end wall 708 to cause the disinfectant applicator 812 to disinfect the head of the NC by application of the disinfectant along with an engagement of the disinfectant applicator 812 with the head of the NC. The body 702 of the carrier 700 can include a convexity 724 that is sized and shaped to generally follow the contours of the septum region of the head of the NC, which promotes compression of the disinfectant applicator 812 with the head of the NC.

From the cross-sectional view of the single use cap 300 shown in FIG. 6, the set of sleeve ejecting edges 720 can be seen positioned in proximity to the rolled edge 806' of the elastomeric sleeve 800 so that a depressing force received on the sealing ring 714 in the direction of arrows 600 can cause the set of sleeve ejecting edges 720 to urge the rolled edge 806' of the elastomeric sleeve 800 away from the set of flange structures 722.

Figure 7A:
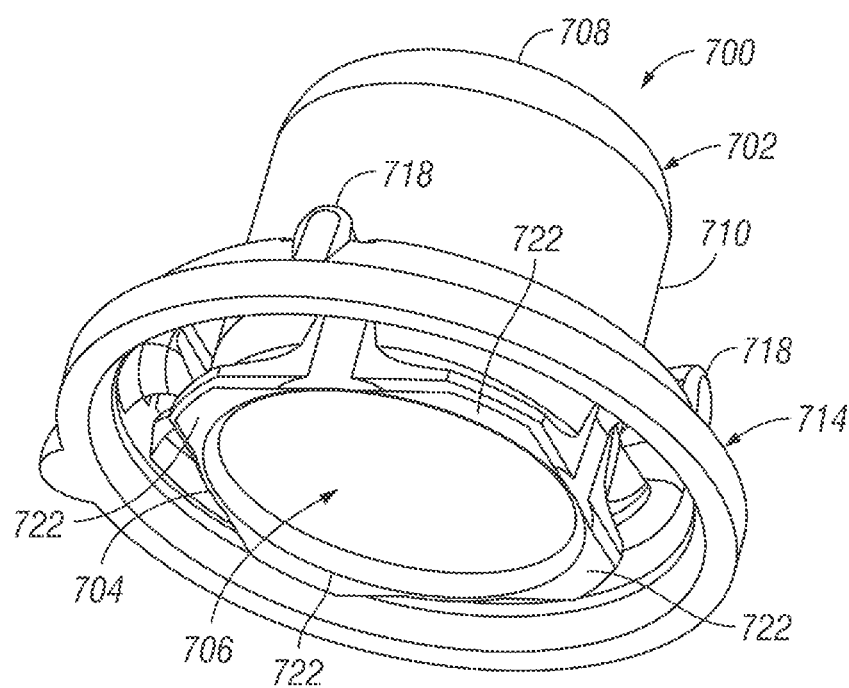
FIGS. 7A and 7B are schematic diagrams showing various views of the carrier of a single use cap in accordance with an illustrative embodiment.
Figure 7B:
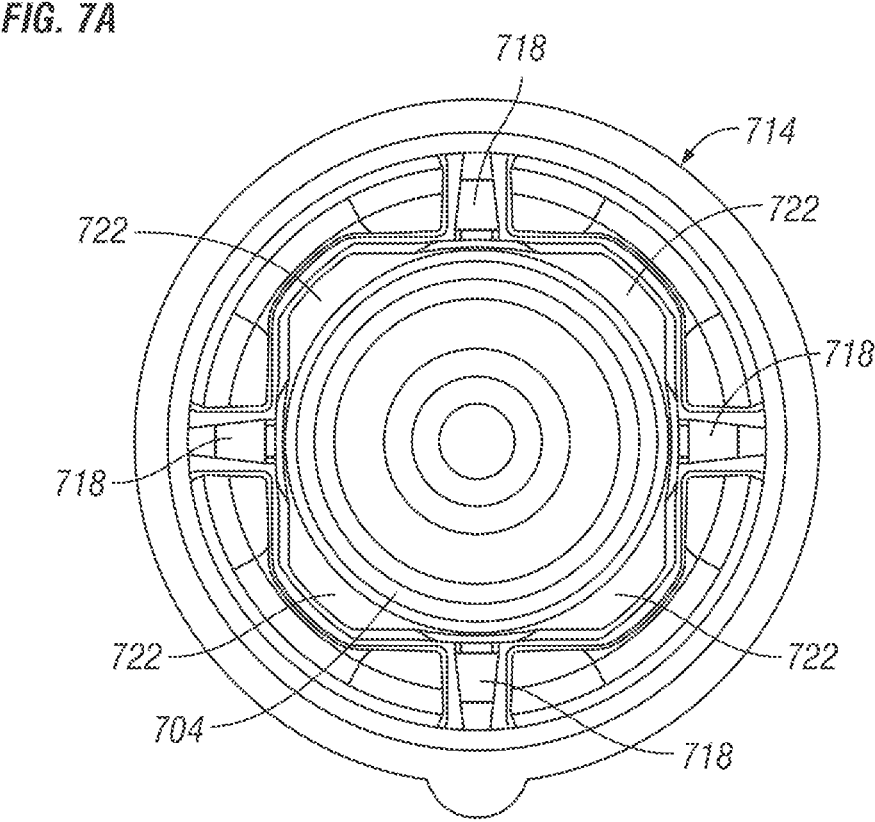

FIGS. 7A and 7B are schematic diagrams showing various views of the carrier of a single use cap in accordance with an illustrative embodiment. In particular, FIG. 7A shows a bottom perspective view of the carrier 700 and FIG. 7B shows a bottom plan view of the single use cap 300. The carrier 700 is shown with a sealing ring 714 flexibly attached to the body 702 by a set of connecting arms 718. The body 702 has an end wall 708 separated from the base 704 by a cylindrical sidewall 710. The base 704 of the body 702 defines an opening that leads into a cavity 712. Projecting outwardly from the sidewall 710 at the base 704 of the body 702 is one or more flange structures 722 configured to engage with an elastomeric sleeve 800 to span the opening 706.

Figures 8A, 8B:
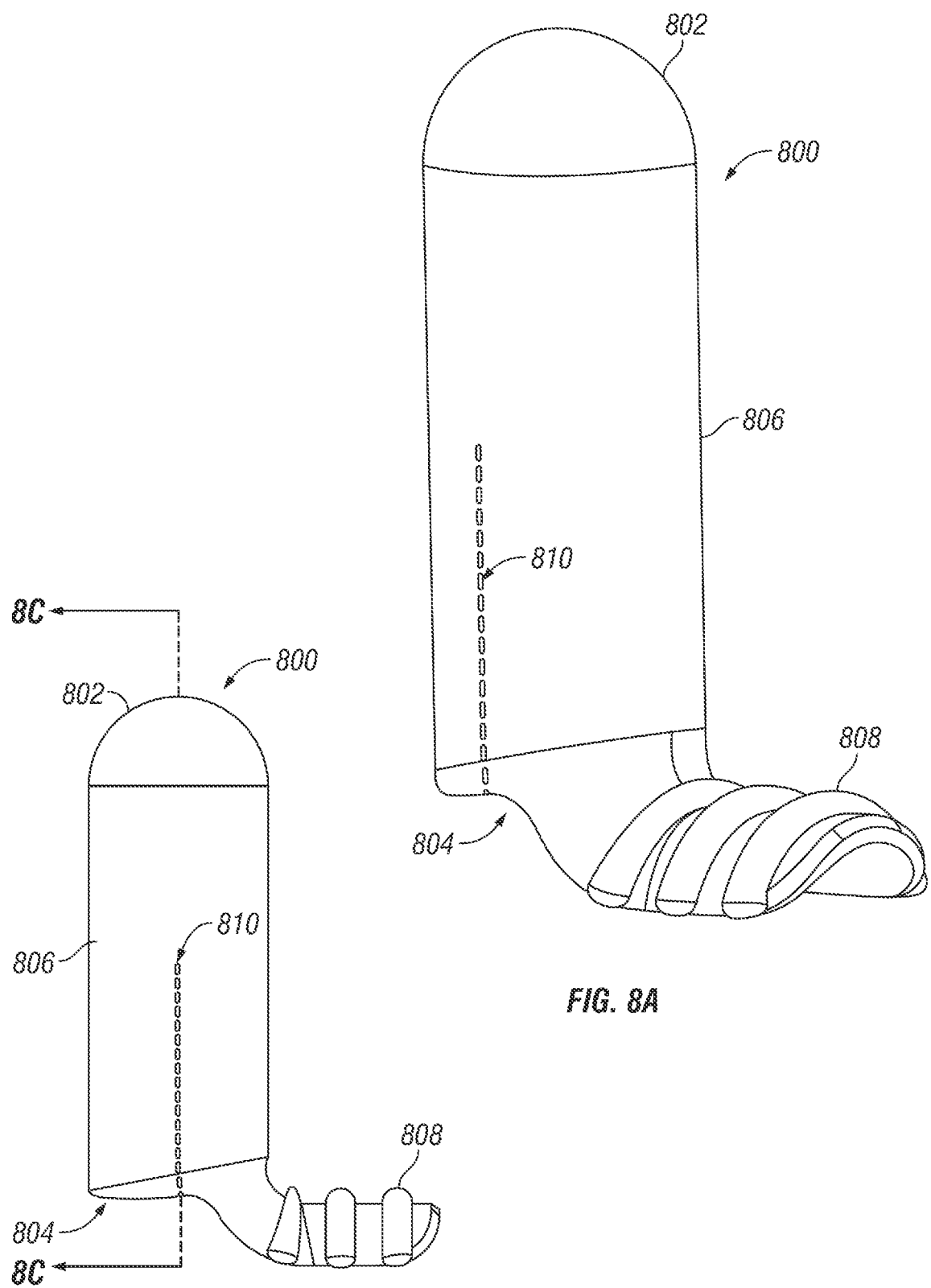
FIGS. 8A-8C are schematic diagram showing various views of an elastomeric sleeve in accordance with an illustrative embodiment.
Figure 8C:
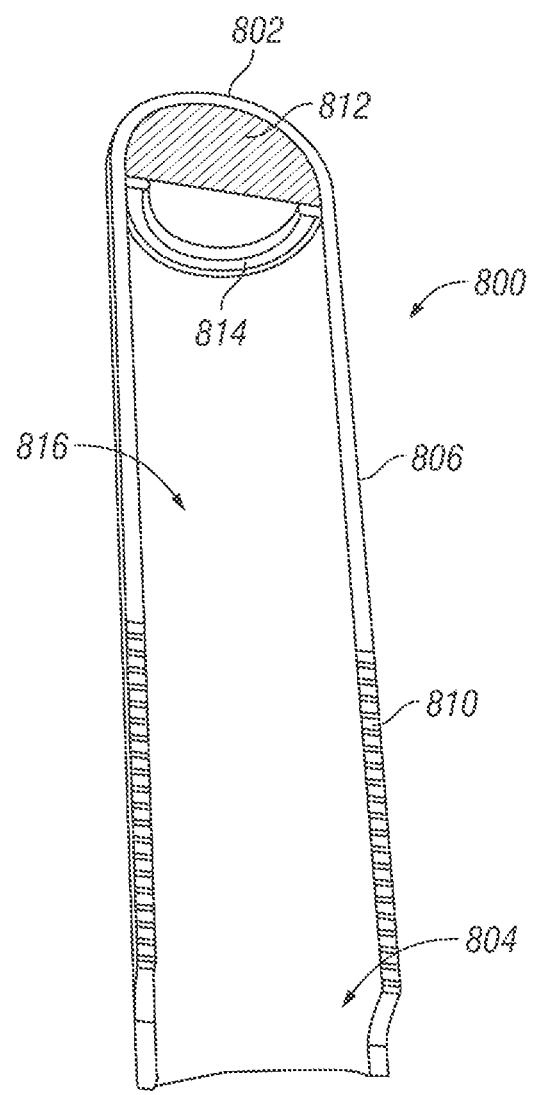

FIGS. 8A-8C are schematic diagrams showing various views of an elastomeric sleeve in accordance with an illustrative embodiment. The elastomeric sleeve 800 is a removable covering that can be applied to the head of a needleless connector by a carrier, such as carrier 700 in FIGS. 7A and 7B. With particular reference to FIGS. 8A and 8B, the elastomeric sleeve 800 can have a generally tubular form with a curved end wall 802 at a distal end which is separated from an opening 804 at a proximal end by an elastic sidewall 806. The elastomeric sleeve 800 can be formed from a flexible, stretchable material that can be stretched to frictionally fit around the head of a conventional NC. Thus, at least the opening 804 of the elastomeric sleeve 800 should have a diameter that is smaller than the diameter of the head of the conventional NC.

In this illustrative embodiment, the elastomeric sleeve 800 includes a pull tab 808 that extends from the proximal end of the elastic sidewall 806. The pull tab 808 provides a graspable feature to aid in removal of the elastomeric sleeve 800 once it has been installed onto the head of an NC. The elastomeric sleeve 800 can also include a set of perforations 810 extending at least partially the length of the elastic sidewall 806 from the proximal end towards the distal end. The set of perforations facilitate tearing of the elastic sidewall 806 for removal of the elastomeric sleeve 800 from the NC when a removing force is applied to the elastomeric sleeve 800, particularly at the pull tab 808. The resultant tear in the elastic sidewall 806 can serve as an obvious indicator that the elastomeric sleeve 800 has been used, as well as serving as a means to prevent reapplication of the elastomeric sleeve 800 to the head of an NC.

FIG. 8C is a cross-sectional view of FIG. 8B taken along line 8C-8C. The set of perforations 810 is formed into the elastic sidewall 806 to cause the elastic sidewall 806 to tear more easily and in a predictable manner. In some embodiments, the end wall 802 at the distal end of the elastomeric sleeve 800 houses a disinfectant applicator 812 configured to disinfect the head of a NC when the elastomeric sleeve 800 is properly secured to the head of an NC. The disinfectant applicator 812 can be formed from an absorbent material, like sponge or ball of cotton, which dispense disinfectant onto the head of an NC when the disinfectant applicator 812 is compressed between the end wall 708 of the carrier 700 and the head of an NC. The disinfectant applicator 812 can be secured at a distal end of the elastomeric sleeve 800 by a retaining ring 814 that projects radially inward to reduce an effective diameter of the cavity 816 bounded by the elastic sidewalls 806.

In another embodiment, the disinfectant applicator 812 can be a reservoir maintained at the end of the elastomeric sleeve 800 and sealed by a frangible membrane that causes the disinfectant to be released onto the head of the NC when the disinfectant applicator 812 is exposed to a compressive force between the end wall 708 of the carrier and the head of an NC.

Figure 9A:
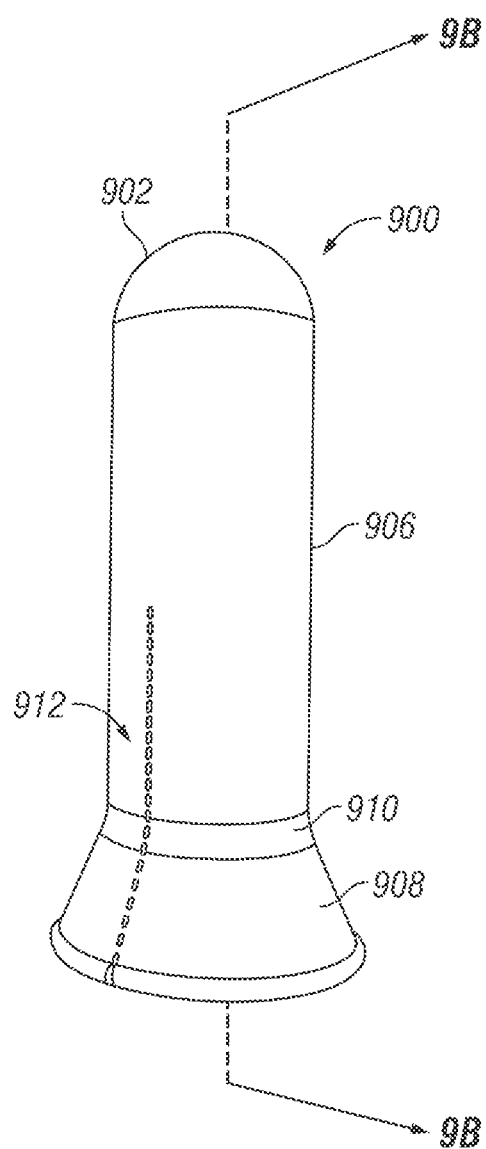
FIGS. 9A and 9B are schematic diagrams showing various views of an elastomeric sleeve in accordance with another illustrative embodiment.
Figure 9B:
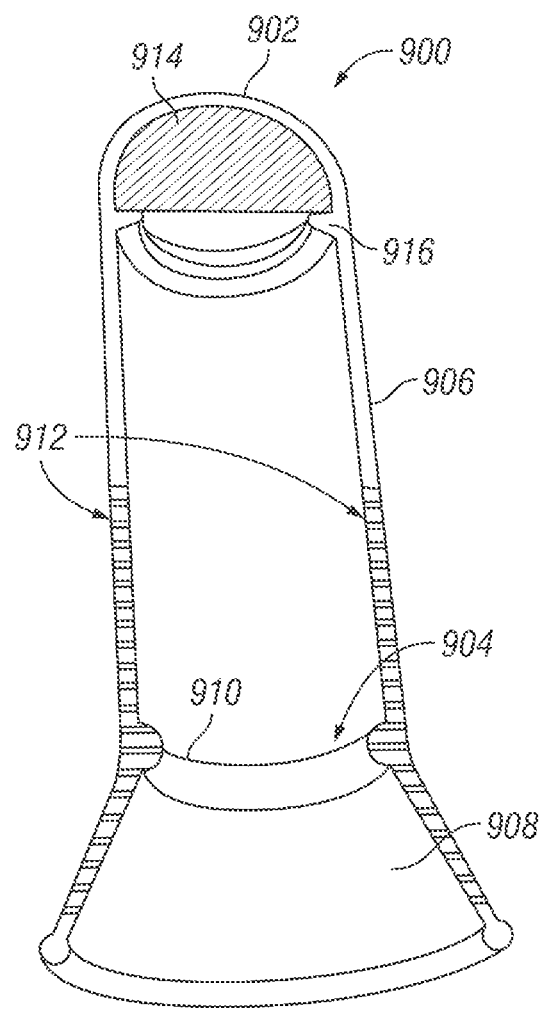

FIGS. 9A and 9B are schematic diagrams showing various views of an elastomeric sleeve in accordance with another illustrative embodiment. The elastomeric sleeve 900 is a removable covering that can be applied to the head of a needleless connector by a carrier, such as carrier 700 in FIG. 7A, as previously described. With reference to FIG. 9A, it can be seen that the elastomeric sleeve 900 can have a generally tubular form with a curved end wall 902 at a distal end which is separated from an opening 904 at a proximal end by an elastic side wall 906. The opening 904 is defined by a flared skirt 908 which is a graspable feature that facilitates removal of the elastomeric sleeve 900 from the head of a needleless connector. In one or more embodiments, the flared skirt 908 narrows to a neck 910 having a diameter that is smaller than the diameter of the head of a conventional NC. Additionally, the elastomeric sleeve 900 can be formed from a flexible, stretchable material so that the application of the elastomeric sleeve 900 to an NC will cause the elastomeric sleeve 900 to frictionally engage the outer surface of the NC.

The elastomeric sleeve 900 can also include a set of perforations 912 extending at least partially the length of the elastic sidewall 906 from the proximal end towards the distal end. The set of perforations facilitate tearing of the elastic sidewall 906 for removal of the elastomeric sleeve 900 from the head of an NC when a removing force is applied to the elastomeric sleeve 900, particularly at the skirt 908. The resultant tear in the elastic sidewall 906 can serve as an obvious indicator that the elastomeric sleeve 900 has been used, as well as serving as a means to prevent reapplication of the elastomeric sleeve 900 to the head of an NC.

FIG. 9B is a cross-sectional view of FIG. 9A taken along line 9B-9B. In the depicted embodiment, the flared skirt 908 narrows to a neck 910 with a diameter that is generally consistent throughout the length of the elastomeric sleeve 900. The set of perforations 912 is formed into the sidewall 906 of the elastomeric sleeve 900 causes the elastic sidewall 906 to tear more easily and in a more predictable manner. In some embodiments, a disinfectant applicator 914 is housed at the distal end of the elastomeric sleeve 900, secured by a retaining ring 916. The disinfectant applicator 914 can be formed from an absorbent material, like sponge or cotton, which can be dispensed onto the head of an NC when the disinfectant applicator 914 is compressed between the end wall 902 of the carrier 700 and the head of an NC. In another embodiment, the disinfectant applicator 914 can be a reservoir maintained at the end of the elastomeric sleeve 900 and sealed by a frangible membrane that causes the disinfectant to be released onto the head of the NC when the disinfectant applicator 914 is exposed to a compressive force between the end wall 708 of the carrier 700 and the head of an NC.

Figure 10A:
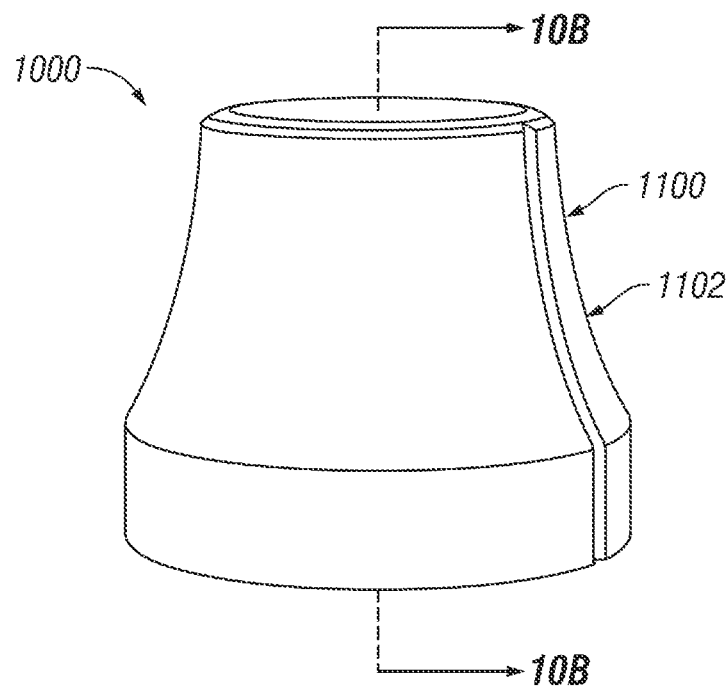
FIGS. 10A and 10B are schematic diagrams providing varying perspective views of a single use cap according to an illustrative embodiment.
Figure 10B:
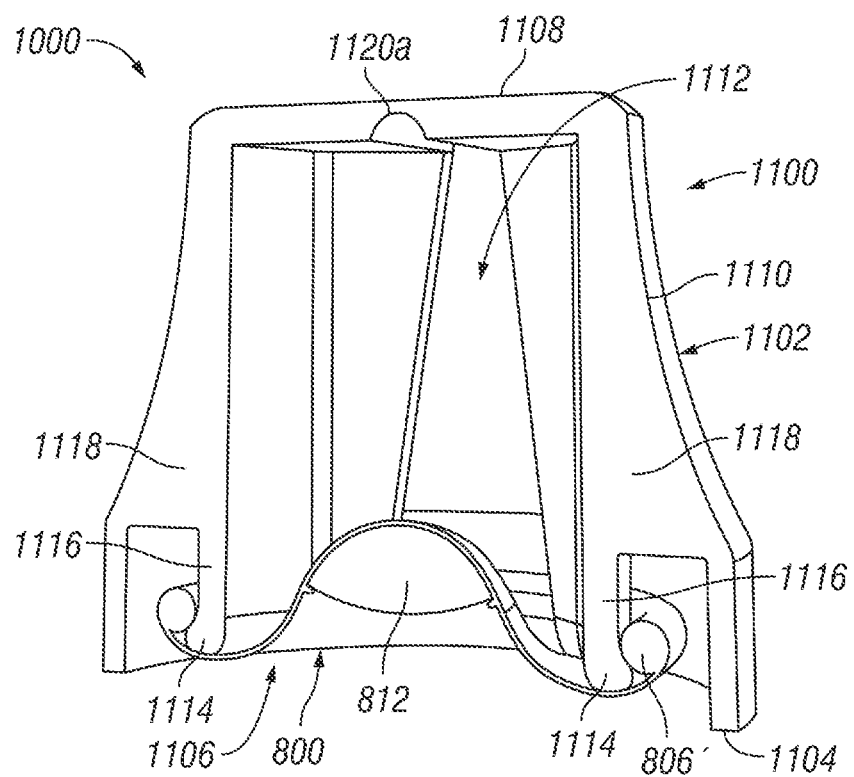

FIGS. 10A and 10B are schematic diagrams providing various views of a single use cap according to another illustrative embodiment. The single use cap 1000 is generally formed from an elastomeric sleeve, such as elastomeric sleeve 800, releasably coupled to a carrier 1100 that includes a body 1102 with a base 1104 defining an opening 1106 that is separated from an end wall 1108 by a side wall 1110. The opening 1106 leads into a cavity 1112 sized to receive a head of a needleless connector (NC).

With reference to FIG. 10A, the carrier 1100 has a generally frusto-conical shape. The elastomeric sleeve 800 can be exposed at the flared base 1104 so that when the carrier 1100 is coupled with the head of a needleless connector, such as NC 100 in FIG. 1, the elastomeric sleeve 800 can be disengaged from the carrier 1100 and transferred to the head of the NC. Subsequent removal of the carrier 1100 from the head of the NC leaves only the elastomeric sleeve behind. When the elastomeric sleeve 800 is engaged with the needleless connector, the elastomeric sleeve 800 is frictionally fit around the head of the needleless connector so that the opening of the needleless connector is sealed within a cavity of the elastomeric sleeve 800.

FIG. 10B is a cross-sectional view of single use cap 1000 depicted in FIG. 10A, taken along 10B-10B. The carrier 1100 includes a set of flange structures 1114 suspended within the cavity 1112 by a corresponding set of flange hangers 1116. In this illustrative embodiment, the set of flange hangers 1116 includes two flange hangers 1116, each of which are suspended from the inner surface of the end wall 1108. In addition, or in the alternative, the set of flange hangers 1116 can be mounted to the inner surface of the sidewall 1110, such as by mounts 1118. In either embodiment, each of the set of flange hangers 1116 are disposed on opposing halves of the carrier 1100, the opposing halves defined by a hinge 1120 that allows the body 702 of the carrier 1100 to flex inwardly. The hinge 1120 is formed from hinge portions 1120a, 1120b, and 1120c. The inward flexation of the opposing halves of the body 1102 is achieved by a compressive force exerted on the outside of the body 1102 in a direction and location depicted and described in more detail in FIG. 11B that follows. The mounts 1118 translate the compressive force exerted on the outside of the body 1102 to cause the set of flange hangers 1116 to also flex inwardly.

The elastomeric sleeve 800 is mounted to the set of flange structures 1114 of the carrier 1100 in a similar manner that the elastomeric sleeve 800 is mounted to the set of flange structures 722 of the carrier 700 shown in FIGS. 7A and 7B. For example, the elastic sidewall 806 of the elastomeric sleeve 800 can be rolled up to form a rolled sidewall portion 806' that can be stretched out between the opposing flange structures 1114 to span the opening 1106. To ensure that the elastomeric sleeve 800 can be disengaged from the set of flange structures 1114, each of the flange hangers 1116 is engaged with one of the halves of the body 1102 so that the compressive force applied to the exterior of the body 1102 causes each of the set of flange hangers 1116 to flex inwardly at the hinge 1120. As the halves of the body 1102 to flex inwardly at the hinge 1120, the elastomeric sleeve 800 can be released from the set of flange structures 1114.

The hinge 1120 is a trough-like structure recessed into the end wall 1108 and in some embodiments into the sidewall 1110 as well. In the depicted embodiment, hinge 1120a is recessed into the inner surface of the end wall 1108 and the hinge 1120b and 1120c are recessed into the outer surfaces of the sidewall 1110 at opposing sides of the body 1102, as can be seen in FIG. 11B.

During use, the head of an NC is inserted through the opening 1106 of the base 1104 and at least partially into the cavity 1112 of the carrier 1100 to contact the interior surface of the elastomeric sleeve 800, as described in more detail in FIG. 6. As the head of the NC progresses into the cavity 1112, the elastomeric sleeve 800 begins to unroll to detach from the set of flange structures 1114. A pressing force can also be applied to the external surface of the carrier 1100 in the direction of arrows 1000, depicted in FIG. 11B, which causes the elastomeric sleeve 800 to detach from the set of flange structures 1114. Detachment of the elastomeric sleeve 800 transfers the elastomeric sleeve 800 to the head of the NC that is at least partially inserted into the cavity 1112 of the carrier 1100.

Although not depicted, a sealing membrane can be adhered to the base 1104 of the single use cap 1000 to prevent contamination of the elastomeric sleeve 800 and to prevent evaporation of disinfectant soaked into the disinfectant applicator. The sealing membrane can be the sealing membrane 400 in FIG. 4, or a lid that is frictionally engaged to the base 1104 of the single use cap 1000.

Figure 11A:
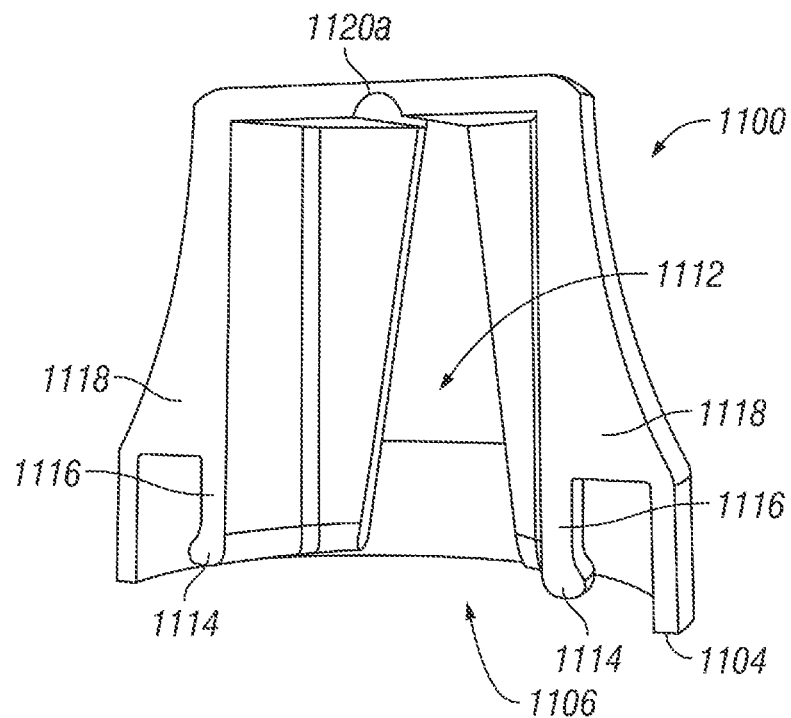
FIGS. 11A and 11B are schematic diagrams of another elastomeric sleeve of a single use cap according to an illustrative embodiment.
Figure 11B:
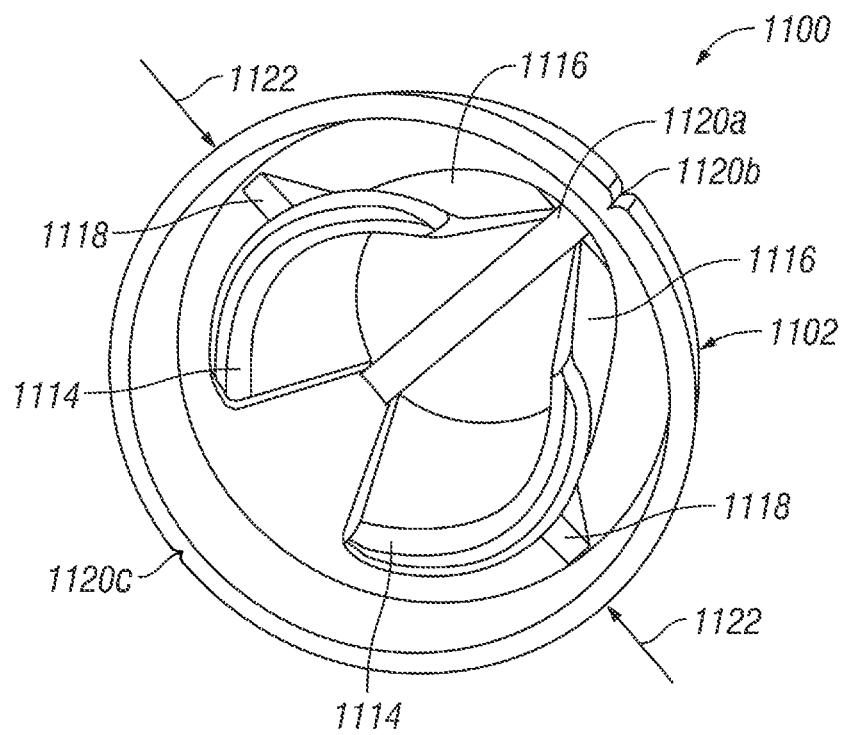

FIGS. 11A and 11B are schematic diagrams of various views of a carrier according to an illustrative embodiment. In particular, FIG. 11A depicts a cross-sectional view of the carrier 1100 from FIG. 10B, but without the elastomeric sleeve 800. FIG. 11B is a perspective view of the carrier 1100 looking into the cavity 1112 from the opening 1106 in the base 1104. As can be seen, the set of flange hangers 1116 are suspended from the end wall 1108 and connected to the sidewall 710 by mounts 1118. The set of flange structures 1114 are formed at the ends of the set of flange hangers 1116. Pressing forces in the direction of arrows 1122 cause the body 1102 of the carrier 1100 to flex inwardly along the hinge 1120, which in turn causes the set of flange hangers 1116 to flex inwardly contemporaneously. As a result, an elastomeric sleeve suspended across opening 1106 on the set of flange structures 1114 will be disengaged from the carrier 1100.

Figure 12A:
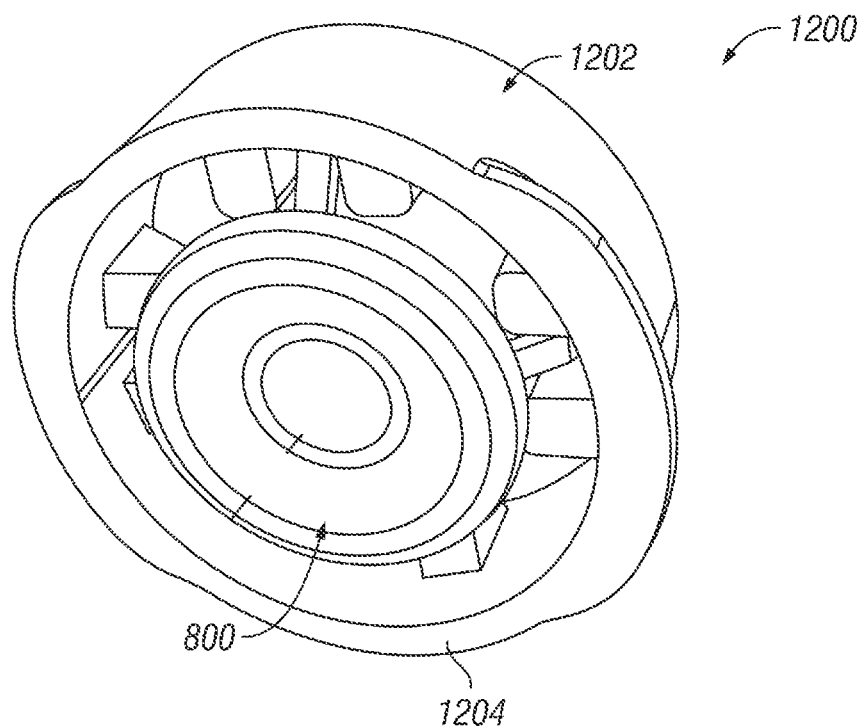
FIGS. 12A and 12B are schematic diagrams providing perspective views of a single use cap according to an illustrative embodiment.
Figure 12B:
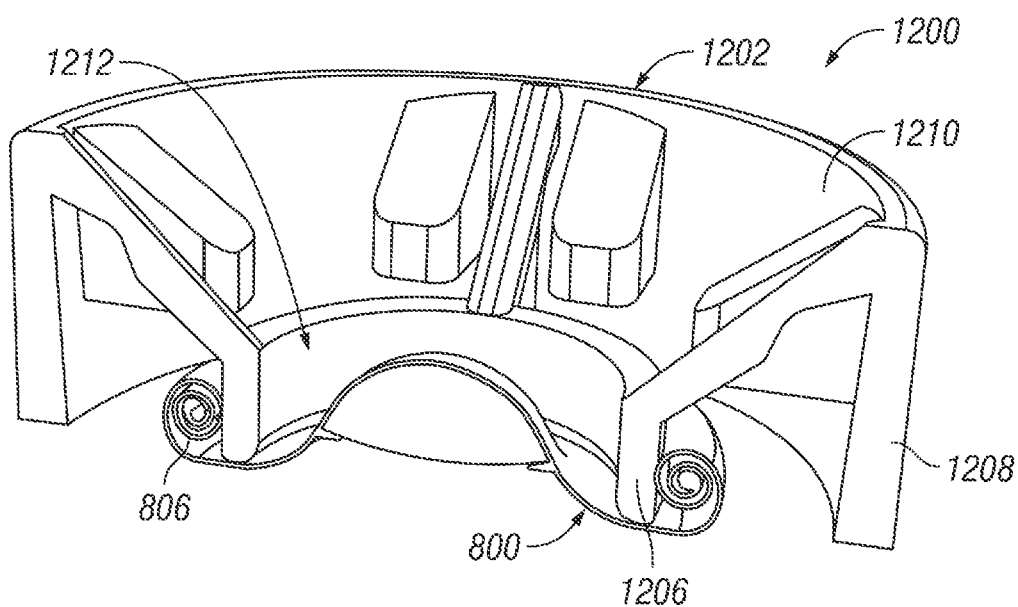

FIGS. 12A and 12B are schematic diagrams providing perspective views of another single use single use cap according to an illustrative embodiment. The single use cap 1200 is formed from a carrier 1202 and an elastomeric sleeve, such as elastomeric sleeve 800 in FIG. 8 or elastomeric sleeve 900 in FIG. 9. FIG. 12A is a perspective view of the single use cap 1200 from the base 1204 and FIG. 12B is a partial section view of the single use cap 1200 which depicts the engagement of the elastomeric sleeve 800 with the carrier 1202.

In this illustrative embodiment in FIG. 12, the carrier 1202 is formed from an outer side wall 1208 connected to an inner side wall 1206 by an end wall 1210. The inner side wall 1206 defines an aperture 1212 that is concentric with the inner side wall 1206 and the outer side wall 1208. When the single use cap 1200 is in the unused configuration, the elastomeric sleeve 800 is in a rolled-up configuration and engaged with the inner side wall 1206 to span the mouth of the aperture 1212.

To apply the elastomeric sleeve 800 to the head of an NC, the head of the NC is inserted into the aperture 1212 from the base 1204. As the head of the NC proceeds into and through the aperture 1212, the elastomeric sleeve 800 engages with the head, causing the side walls 806 of the elastomeric sleeve 800 to unroll and disengage from the inner sidewall 1206 and transfer onto the head of the NC. The carrier 1202 can be withdrawn from the head of the NC to leave the elastomeric sleeve 800 securely engaged around the head of the NC.

Figure 13:
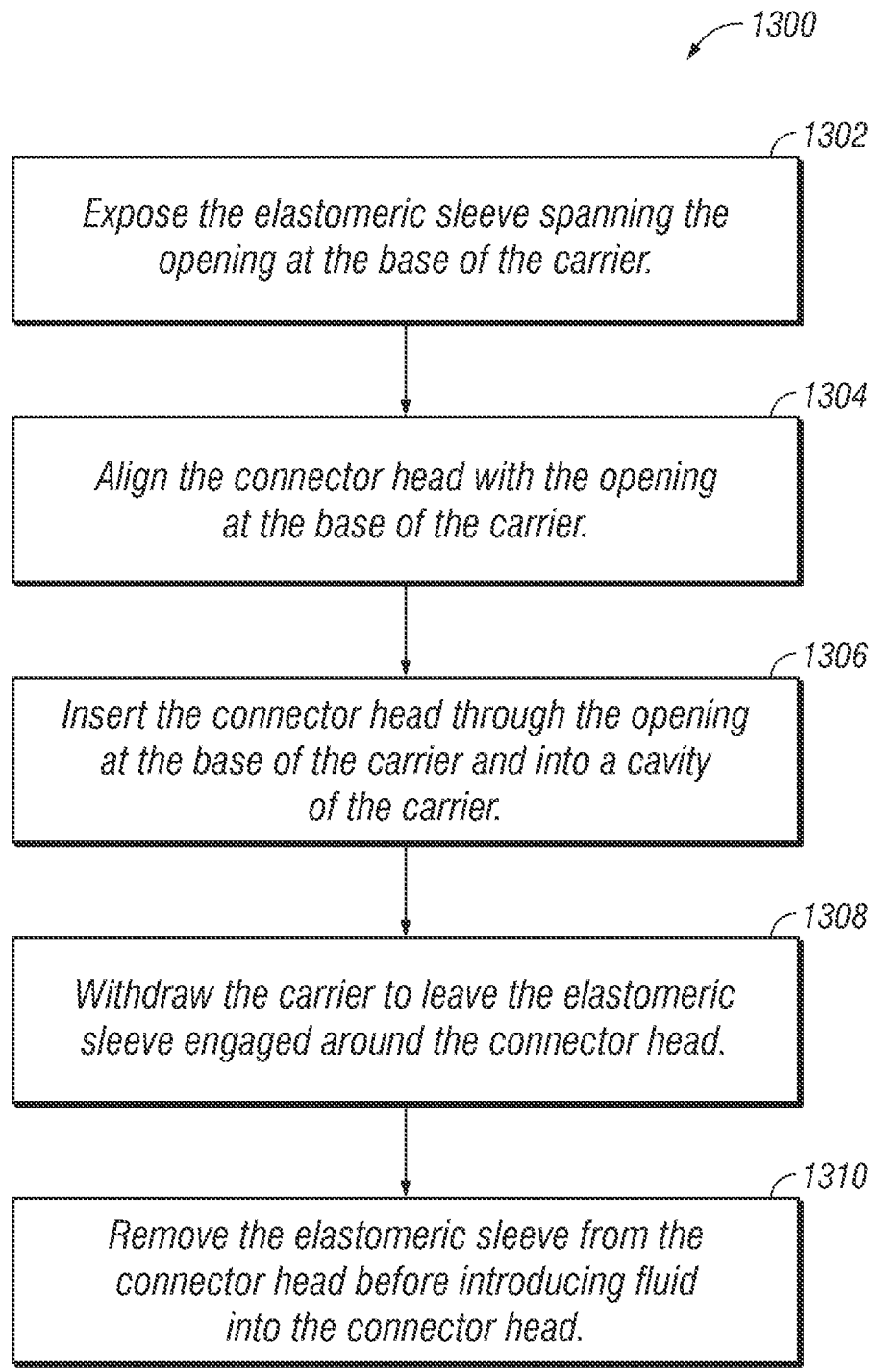
FIG. 13 is a flowchart of a process for using a novel single use cap in accordance with an illustrative embodiment.

FIG. 13 is a flowchart of a process for using a single use single use cap according to an illustrative embodiment. The steps of flowchart 1300 can be carried out on a single use single use cap having an elastomeric sleeve releasably coupled to a carrier comprising a body including a base defining an opening that is separated from an end wall by a side wall, the opening leads into a cavity sized to receive a head of an NC, such as NC 300 in FIG. 3.

Flowchart 1300 begins at step 1302 by exposing the elastomeric sleeve spanning the opening at the base of the carrier. In one embodiment, the elastomeric sleeve is exposed by removing a sealing membrane from a sealing ring connected to the body of the carrier by a set of connecting arms.

In step 1304, the head of the NC is aligned with the opening at the base of the carrier.

In step 1306, the head of the NC is inserted through the opening at the base of the carrier and into the cavity to cause the elastomeric sleeve to disengage from the carrier and transfer to the head of the NC. In some embodiments, inserting the head of the NC through the opening at the base of the carrier and into the cavity introduces a disinfectant to the head of the NC. In a more particular embodiment, the disinfectant is introduced to the head of the NC by inserting the head of the NC into the cavity until an inner surface of the end wall of the carrier compresses a disinfectant applicator secured inside elastomeric sleeve at its distal end.

In some embodiments, flowchart 1300 includes step 1308 where the carrier is removed from the NC to leave the elastomeric sleeve frictionally engaged around the head of the NC. In one or more of these embodiments, removal of the carrier from the NC to leave the elastomeric sleeve frictionally engaged around the head of the NC includes the additional step of triggering a set of secondary ejection features that facilitates the release off the elastomeric sleeve from the carrier. In one embodiment, the sleeve ejection feature is a sleeve ejection edge of a sealing ring triggered by application of a depressing force on the sealing ring. In another embodiment, the sleeve ejection feature is a set of flange hangers disposed in the cavity of a single use cap carrier and triggered by application of a compressing force on an exterior surface of the carrier.

In some embodiments, flowchart 1300 also includes step 1310 of removing the elastomeric sleeve from the head of the NC before introducing a fluid into the NC via the head of the NC. The step of removing the elastomeric sleeve can include the additional steps of grasping a grasping surface deviating outwardly from the elastic sidewall of the elastomeric sleeve and exerting a removing force that causes the elastic sidewall to tear along a set of perforations extending from the opening at the proximal end towards the end wall at the distal end.

In some embodiments, the elastomeric sleeve is releasably coupled to one or more flange structures projecting radially outwardly from the sidewall around the opening at the base of the carrier so that inserting the head of the NC through the opening at the base of the carrier and into the cavity causes the elastomeric sleeve to disengage from the one or more flange structures. In a more particular embodiment, the elastomeric sleeve is releasably coupled to the one or more flange structures while in a shortened state, and the elastomeric sleeve disengages from the one or more flange structures in response to attaining elongated state.

Although embodiments of the invention have been described with reference to several elements, any element described in the embodiments described herein are exemplary and can be omitted, substituted, added, combined, or rearranged as applicable to form new embodiments. A skilled person, upon reading the present specification, would recognize that such additional embodiments are effectively disclosed herein. For example, where this disclosure describes characteristics, structure, size, shape, arrangement, or composition for an element or process for making or using an element or combination of elements, the characteristics, structure, size, shape, arrangement, or composition can also be incorporated into any other element or combination of elements, or process for making or using an element or combination of elements described herein to provide additional embodiments.

Additionally, where an embodiment is described herein as comprising some element or group of elements, additional embodiments can consist essentially of or consist of the element or group of elements. Also, although the open-ended term "comprises" is generally used herein, additional embodiments can be formed by substituting the terms "consisting essentially of" or "consisting of."

While this invention has been particularly shown and described with reference to preferred embodiments, it will be understood by those skilled in the art that various changes in form and detail may be made therein without departing from the spirit and scope of the invention. The inventors expect skilled artisans to employ such variations as appropriate, and the inventors intend the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

We claim:

1. A single use cap comprising:
    a carrier with a body including a base that defines an opening separated from an end wall by a side wall, wherein the opening leads into a cavity sized to receive a connector head; and
    an elastomeric sleeve releasably coupled to the carrier to span and seal the opening, wherein the elastomeric sleeve is configured to be transferred to the connector head upon insertion of the head through the opening and at least partially into the cavity.

2. The single use cap of claim 1, wherein the carrier further comprises one or more flange structures disposed around the opening of the carrier, and wherein the elastomeric sleeve is engaged with the one or more flange structures to span the opening.

3. The single use cap of claim 2, wherein the elastomeric sleeve is configured to be engaged with the one or more flange structures while in a partially rolled configuration, and wherein the elastomeric sleeve is configured to be disengaged from the one or more flange structures during a transition into an unrolled configuration.

4. The single use cap of claim 1, wherein the carrier further comprises:
a sealing ring connected to the body by a set of connecting arms, wherein:
the sealing ring is coaxial with the base;
the sealing ring has a sealing surface configured to be sealed against a sealing membrane; and
the sealing surface is offset from the base of the carrier in an axial direction.

5. The single use cap of claim 4, further comprising:
a sealing membrane engaged with the elastomeric sleeve and the sealing surface of the sealing ring.

6. The single use cap of claim 4, wherein the sealing ring further comprises:
a sleeve ejection feature at least partially circumscribing the body of the carrier, wherein the sleeve ejection feature is configured to engage with the elastomeric sleeve in response to receiving a depressing force on the sealing ring.

7. The single use cap of claim 1, wherein:
the elastomeric sleeve is an elongated tubular structure with an end wall at a distal end and an opening at a proximal end; and
an elastic side wall separating the end wall from the opening.

8. The single use cap of claim 7, wherein the elastomeric sleeve further comprises:
a disinfectant applicator housed within a cavity defined by the elastic side wall, secured at the distal end between the end wall and a retaining ring.

9. The single use cap of claim 7, further comprising:
a grasping surface deviating outwardly from the elastic side wall at the proximal end.

10. The single use cap of claim 7, wherein elastomeric sleeve further comprises:
a set of perforations in the elastic sidewall and extending from the opening at the proximal end towards the end wall at the distal end.

11. A method of using a single use cap comprising an elastomeric sleeve releasably coupled to a carrier comprising a body including a base defining an opening that is separated from an end wall by a side wall, wherein the opening leads into a cavity sized to receive a connector head, the method comprising:
exposing the elastomeric sleeve spanning the opening at the base of the carrier;
aligning the connector head with the opening at the base of the carrier;
inserting the connector head through the opening at the base of the carrier and into the cavity to cause the elastomeric sleeve to disengage from the carrier and transfer to the connector head.

12. The method of claim 11, further comprising:
withdrawing the carrier to leave the elastomeric sleeve frictionally engaged around the connector head.

13. The method of claim 12, wherein withdrawing the carrier to leave the elastomeric sleeve frictionally engaged around the connector head further comprises:
depressing the sealing ring to cause a set of sleeve ejection features to engage with the elastomeric sleeve to cause the elastomeric sleeve to achieve uninstalled configuration.

14. The method of claim 12, wherein the connector head is a head of a needleless connector (NC), the method further comprising:
removing the elastomeric sleeve from the head of the NC before introducing a fluid into the NC via the head of the NC.

15. The method of claim 14, wherein removing the elastomeric sleeve further comprises:
grasping a grasping surface deviating outwardly from the elastic sidewall of the elastomeric sleeve; and
exerting a removing force that causes the elastic sidewall to tear along a set of perforations extending from the opening at the proximal end towards the end wall at the distal end.

16. The method of claim 11, wherein exposing the elastomeric sleeve comprises:
removing a sealing membrane from a sealing ring connected to the body by a set of connecting arms, wherein:
the sealing ring is coaxial with the base;
the sealing ring has a sealing surface configured to be sealed against a sealing membrane; and
the sealing surface is offset from the base of the carrier in an axial direction.

17. The method of claim 11, wherein the elastomeric sleeve is releasably coupled to one or more flange structures disposed around the opening of the carrier, and wherein the elastomeric sleeve is engaged with the one or more flange structures to span the opening, and wherein inserting the connector head through the opening at the base of the carrier and into the cavity causes the elastomeric sleeve to initiate disengagement from one or more flange structures.

18. The method of claim 17, wherein the elastomeric sleeve releasably coupled to the one or more flange structures while in a partially rolled configuration, and wherein the elastomeric sleeve is configured to be disengaged from the one or more flange structures during a transition into an unrolled configuration.

19. The method of claim 11, wherein inserting the connector head through the opening at the base of the carrier and into the cavity further comprises:
introducing a disinfectant to the connector head.

20. The method of claim 19, wherein the disinfectant is introduced to the connector head by inserting the connector head into the cavity until a disinfectant applicator housed within the elastomeric sleeve is compressed between the end wall of the carrier and the connector head.

* * * * *